United States Patent
Lee et al.

(10) Patent No.: US 9,974,504 B2
(45) Date of Patent: May 22, 2018

(54) X-RAY DEVICE AND METHOD FOR CONTROLLING X-RAY IRRADIATION AREA USING THE SAME

(75) Inventors: Byeong Won Lee, Gyeonggi-do (KR); Jae Hwa Moon, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 545 days.

(21) Appl. No.: 13/546,624

(22) Filed: Jul. 11, 2012

(65) Prior Publication Data

US 2013/0022172 A1 Jan. 24, 2013

(30) Foreign Application Priority Data

Jul. 18, 2011 (KR) .................. 10-2011-0070932
Nov. 10, 2011 (KR) .................. 10-2011-0116717

(51) Int. Cl.
*A61B 6/00* (2006.01)
*A61N 5/10* (2006.01)
*H05G 1/26* (2006.01)

(52) U.S. Cl.
CPC .............. *A61B 6/465* (2013.01); *A61B 6/462* (2013.01); *A61B 6/463* (2013.01); *A61B 6/469* (2013.01); *A61B 6/542* (2013.01); *A61B 6/548* (2013.01); *A61N 2005/1074* (2013.01); *H05G 1/26* (2013.01)

(58) Field of Classification Search
USPC ....... 378/63, 64, 65, 68, 162, 165, 207, 205; 382/147, 151
See application file for complete search history.

(56) References Cited

U.S. PATENT DOCUMENTS

| 5,539,798 | A | 7/1996 | Asahina et al. | |
|---|---|---|---|---|
| 6,447,163 | B1 * | 9/2002 | Bani-Hashemi | A61B 6/08 378/205 |
| 6,795,526 | B2 * | 9/2004 | Kump | A61B 6/544 378/116 |

(Continued)

FOREIGN PATENT DOCUMENTS

| CN | 1476812 A | 2/2004 |
|---|---|---|
| CN | 101035466 A | 9/2007 |

(Continued)

OTHER PUBLICATIONS

Communication of Notice of Opposition, dated Feb. 16, 2015, issued by the European Patent Office in European Application No. 12174970.9.

(Continued)

*Primary Examiner* — Kiet T Nguyen
(74) *Attorney, Agent, or Firm* — Sughrue Mion, PLLC

(57) ABSTRACT

An X-ray device includes a camera to image an object and output the image of the object, a display member using a touch screen to display the image of the object output from the camera, and an X-ray irradiation region of the object, an X-ray irradiation region controller to control a region of the object to which an X-ray is irradiated, and a control member to enable the irradiation region controller to control the region of the object to which an X-ray is irradiated according to the X-ray irradiation region, when the X-ray irradiation region is determined, based on the image of the object displayed in the display member.

21 Claims, 14 Drawing Sheets

(56) References Cited

U.S. PATENT DOCUMENTS

| | | | |
|---|---|---|---|
| 7,344,305 | B2 | 3/2008 | Kuzmanovic |
| 7,494,276 | B2* | 2/2009 | Borgmann et al. ............ 378/207 |
| 8,011,829 | B2* | 9/2011 | Sung et al. .................... 378/207 |
| 2002/0012450 | A1* | 1/2002 | Tsujii ............................ 382/103 |
| 2002/0118280 | A1 | 8/2002 | Medlar et al. |
| 2003/0108154 | A1 | 6/2003 | Schmitt |
| 2003/0165216 | A1 | 9/2003 | Walker et al. |
| 2004/0081281 | A1 | 4/2004 | Fadler et al. |
| 2005/0169425 | A1 | 8/2005 | Takasawa |
| 2009/0175413 | A1 | 7/2009 | Sung et al. |
| 2011/0129058 | A1* | 6/2011 | Ulrici et al. ...................... 378/4 |

FOREIGN PATENT DOCUMENTS

| | | |
|---|---|---|
| DE | 10109219 A1 | 9/2002 |
| DE | 10160611 A1 | 6/2003 |
| DE | 10234465 A1 | 2/2004 |
| DE | 102008035412 A1 | 2/2010 |
| DE | 102008050542 A1 | 4/2010 |
| EP | 1382300 A1 | 1/2004 |
| EP | 1 815 794 A1 | 8/2007 |
| EP | 2079083 A2 | 7/2009 |
| JP | 06-217973 A | 8/1994 |
| JP | 10-155778 A | 6/1998 |
| JP | 2003-116845 A | 4/2003 |
| JP | 2008-515476 A | 5/2008 |
| JP | 2010194004 A | 9/2010 |
| JP | 2011072521 A | 4/2011 |
| KR | 10-0850500 B1 | 8/2008 |
| WO | 2007/031945 A2 | 3/2007 |
| WO | 2011080460 A1 | 7/2011 |

OTHER PUBLICATIONS

Communication dated Apr. 22, 2016, issued by the European Patent Office in counterpart European Patent Application No. 12174970.9.

Communication dated Oct. 20, 2016 issued by the State Intellectual Property Office of P.R. China in counterpart Chinese Patent Application No. 201210249662.3.

Communication dated Feb. 27, 2017 issued by the European Patent Office in counterpart European Patent Application No. 12 174 970.9 (Copy of Minutes).

Communication dated Feb. 27, 2017 issued by the European Patent Office in counterpart European Patent Application No. 12 174 970 .9 (Decision on Grant).

Communication dated Apr. 20, 2017 issued by the State Intellectual Property Office of P.R. China in counterpart Chinese Patent Application No. 201210249662.3 (Notification of Granting of Patent Right to Invention).

Communication dated Apr. 20, 2017 issued by the State Intellectual Property Office of P.R. China in counterpart Chinese Patent Application No. 201210249662.3 (Notification of Due Registration Formalities).

Communication dated Jan. 31, 2018, issued by the European Patent Office in counterpart European Patent Application No. 14166106.6.

* cited by examiner

X-RAY DEVICE AND METHOD FOR CONTROLLING X-RAY IRRADIATION AREA USING THE SAME

CLAIM OF PRIORITY

This application claims, pursuant to 35 U.S.C. 119(a), priority to and the benefit of the earlier filing date of Korean Patent Application Nos. 2011-0070932 and 2011-0116717, filed on Jul. 18, 2011 and Nov. 10, 2011, respectively, in the Korean Intellectual Property Office, the disclosures of which are incorporated herein by reference.

BACKGROUND OF THE INVENTION

1. Field of the Invention

The present invention relates to an X-ray device including an X-ray irradiation region controller to control a region to which X-rays are irradiated, and a method for controlling the X-ray irradiation region using the X-ray device.

2. Description of the Related Art

An X-ray device is an apparatus for diagnosing diseases without incising the bodies of animals or patients by irradiating X-rays to animals or patients, detecting the X-rays transmitted into and through the bodies of animals or patients and thereby obtaining an image of an inner structure of the bodies.

Here, an X-ray is an electromagnetic wave having high transmittance irradiated when high-speed electrons collide with an object. Generally, an X-ray tube that emits thermoelectrons includes filaments to generate an X-ray and an electrode to form a strong electric field with a high voltage. When the high voltage generated by a high-voltage supply is applied to the X-ray tube, a filament serving as a cathode emits the thermoelectrons. The emitted thermoelectrons travel in a controlled direction due to the strong electric field and collide with an anode, and an X-ray is generated at the point with a small size where the thermoelectrons collide with the anode.

Generally, an X-ray device includes the X-ray tube to generate X-rays, an X-ray irradiation region controller to control a region to which the X-rays are irradiated and a detector to detect X-rays having passed through an object.

The X-ray irradiation region controller controls the region to which X-rays are irradiated by blocking X-rays with a substance, such as lead or tungsten, to rapidly attenuate the X-rays. The X-ray irradiation region controller includes a structure to irradiate a visible ray to the region to which X-rays are irradiated in order to enable a user to observe an irradiation region of X-rays that cannot be seen by the naked eye. The user observes the X-ray irradiation region by the naked eye through this structure and controls the region of X-rays irradiated to the object by controlling an aperture of an X-ray irradiation region control unit. Such a method has a problem in that a structure, such as a visible light source disposed in the X-ray irradiation region control unit and a reflector to convert an irradiation direction of visible light into an irradiation direction of X-ray, is abnormally disposed, so visible light is irradiated to a region different from the region to which X-rays are irradiated and abnormal X-ray imaging is thus performed. Also, this method has a problem in that imaging is performed in a wider region than required in order to avoid re-imaging due to the difficulty of accurate designation of an X-ray irradiation region and patients are thus exposed to irradiation of unnecessary X-rays from such re-imaging.

SUMMARY OF THE INVENTION

Therefore, it is one aspect of the present invention to provide an X-ray device including a camera to image an object and a display member using a touch screen to display the object image output from the camera and the X-ray irradiation region.

It is another aspect of the present invention to provide a method for controlling an X-ray irradiation region displayed in the display member through a touch gesture.

It is yet another aspect of the present invention to provide a user interface to provide a control environment of the X-ray irradiation region through a predetermined touch gesture.

In accordance with one aspect of the present invention, an X-ray device is provided which includes: a camera to image an object and output the image of the object; a display member to display the image of the object and an X-ray irradiation region of the object; an X-ray irradiation region controller to control a region of the object to which an X-ray is irradiated; and a control member to enable the irradiation region controller to control the region of the object to which an X-ray is irradiated according to the X-ray irradiation region, when the X-ray irradiation region is determined, based on the image of the object displayed in the display member.

The X-ray irradiation region may be determined based on the image displayed in the display member through a user instruction.

The user instruction may include an instruction input through a touch of the X-ray irradiation region displayed in the display member.

The user instruction may include an instruction input through a remote controller, a mouse, an input device, an audio recognition unit and/or a motion recognition unit.

The camera may be mounted on the X-ray irradiation region controller to image the object.

The display member may use a touchscreen and displays information guiding an X-ray imaging of the object in a plurality of regions on the touchscreen, respectively.

The display member may display a previously input list of X-ray imaging parts of the object in order to allow a user to select a specific X-ray imaging part of the object.

The display member may display a value of an assumed or estimated amount of irradiated X-rays according to the size of the X-ray irradiation region.

The display member may display the X-ray irradiation region in the image of the object output from the camera such that the X-ray irradiation region overlaps the image.

The display member may further display another X-ray irradiation region, in addition to a previously displayed X-ray irradiation region, to be overlapped with the image of the object.

In accordance with another aspect of the present invention, a method is provided for controlling an X-ray irradiation region including: displaying an image of the object obtained by a camera of an X-ray device in a display member of the X-ray device; further displaying an X-ray irradiation region in the display member displaying the obtained image, based on the image of the object displayed in the display member; and controlling a region of the object to which an X-ray is irradiated, based on the X-ray irradiation region displayed in the display member.

The controlling of a region of the object to which an X-ray is irradiated, based on the X-ray irradiation region displayed in the display member, may be carried out through a user instruction.

The user instruction may include an instruction input through a touch of the X-ray irradiation region.

The user instruction may include an instruction input through a remote controller, a mouse, an input device, an audio recognition unit and/or a motion recognition unit.

A value of an assumed or estimated amount of irradiated X-rays may be displayed according to the size of the X-ray irradiation region, when the X-ray irradiation region is displayed.

The camera may be mounted in one part of the outside of the X-ray irradiation region controller to image the object.

The display member may use a touchscreen and displays informations guiding X-ray imaging of the object in a plurality of regions on the touchscreen, respectively.

The controlling of a region of the object to which an X-ray is irradiated, based on the X-ray irradiation region displayed in the display member, may be carried out by displaying an X-ray irradiation region controlled by a user instruction on the object image displayed in the display member such that the X-ray irradiation region overlaps the object image and then controlling the region of the object to which the X-ray is irradiated.

The X-ray irradiation region is controlled in an area different from an area to control the irradiation region by displaying the X-ray irradiation region controlled by user instruction on the object image displayed in the display member such that the X-ray irradiation region overlaps the object image.

When the image of the object obtained by the camera of the X-ray device is displayed in the display member of the X-ray device, an X-ray irradiation region to guide control of the X-ray irradiation region may be separately further displayed.

In accordance with another aspect of the present invention, an X-ray image display method is provided which includes: displaying an image of an object obtained by a camera of an X-ray device in a display member; and displaying an X-ray irradiation region of the object determined based on the image of the object displayed in the display member in the image of the object such that the X-ray irradiation region overlaps the image of the object.

The X-ray irradiation region of the object may be determined based on the image of the object displayed in the display member according to a user instruction.

The user instruction may include an instruction input through a touch of the X-ray irradiation region.

The user instruction may include an instruction input through a remote controller, a mouse, an input device, an audio recognition unit and/or a motion recognition unit.

The X-ray image display method may further display only the X-ray irradiation region in response to an adjustment.

The X-ray irradiation region may be moved, magnified, reduced, rotated and/or initialized by a user instruction.

The X-ray image display method may further include displaying a previously input list of X-ray imaging parts of the object to allow a user to select a specific X-ray imaging part of the object.

The X-ray image display method may further include displaying a value of an assumed or estimated amount of irradiated X-rays according to the size of the X-ray irradiation region.

The X-ray image display method may further include displaying information of the object in the display member.

According to the aspects of the present invention, radiography can be more accurately and easily performed by forming an image to guide the position and gesture of a patient in a radiation region.

In addition, radiography can be more rapidly performed by controlling the gesture of the patient, based on the image formed in the irradiation region.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION OF THE INVENTION

Figure 1:
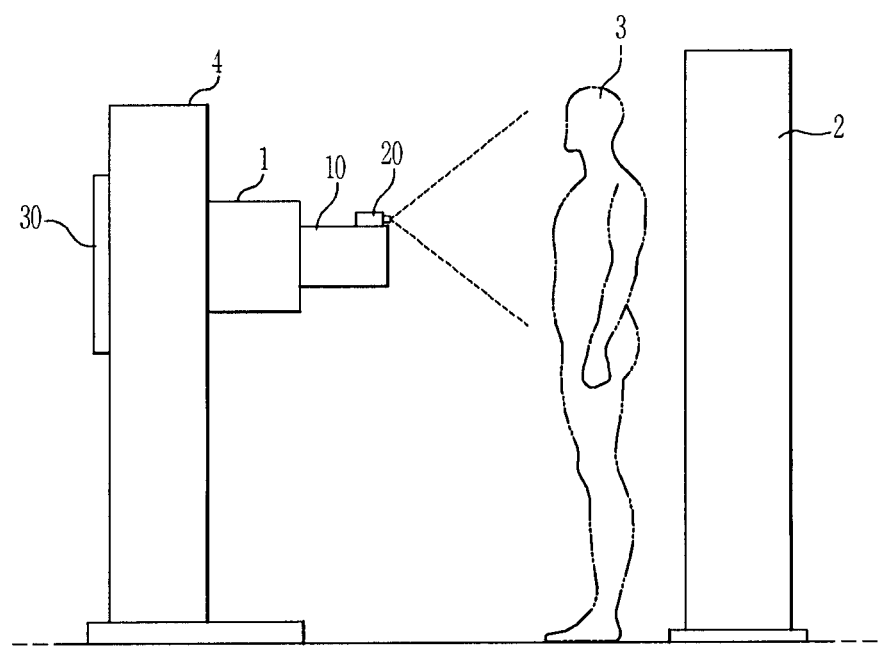
FIG. 1 is a schematic view illustrating an X-ray device according to an exemplary embodiment of the present invention.

Reference will now be made in detail to preferred embodiments of the present invention, examples of which are illustrated in the accompanying drawings, wherein like reference numerals refer to like elements throughout.

Hereinafter, advantages and features of the preferred embodiments of the present invention and methods for accomplishing the same will be easily understood from the detailed description associated with preferred exemplary embodiments and the annexed drawings. However, one or more exemplary embodiments of the present invention may be realized in various forms and the exemplary embodiments described herein are not particularly limited.

In the following description, a detailed explanation of known related functions and constructions may be omitted to avoid unnecessarily obscuring the subject matter of the present invention. This invention may, however, be embodied in many different forms and should not be construed as limited to the exemplary embodiments set forth herein. Also, terms described herein, which are defined considering the functions of the present invention, may be implemented differently depending on user and operator's intention and practice. Therefore, the terms should be understood on the basis of the disclosure throughout the specification. The principles and features of this invention may be employed in varied and numerous embodiments without departing from the scope of the invention.

Furthermore, although the drawings represent exemplary embodiments of the invention, the drawings are not necessarily to scale and certain features may be exaggerated or omitted in order to more clearly illustrate and explain the present invention.

Figure 2:
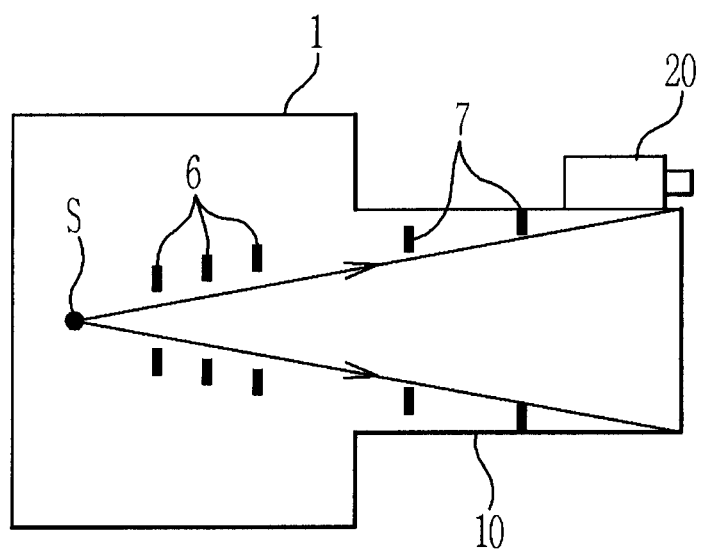
FIG. 2 is a schematic view illustrating a cross-section of an X-ray generator and an X-ray irradiation region controller of the X-ray device according to the exemplary embodiment of the present invention.

FIG. 1 is a schematic view illustrating an X-ray device according to an exemplary embodiment of the present invention. FIG. 2 is a schematic view illustrating a cross-section of an X-ray generator 1 and an X-ray irradiation region controller 10 of the X-ray device according to the exemplary embodiment of the present invention.

The X-ray device according to the exemplary embodiment of the present invention includes the X-ray generator 1, an X-ray irradiation region controller 10 to control an irradiation passage and region of X-rays generated by the X-ray generator 1, a camera 20 adhered to the outer surface of the X-ray irradiation region controller 10 to image an object 3, a detector 2 to detect the X-rays having passed through the object 3, a guide member 4 to guide movement of the X-ray generator 1, and a display member 30 to provide a user with information for X-ray imaging.

The X-ray generator 1 generates an X-ray, which is an electromagnetic wave that has a short wavelength and high transmittance, emitted when electrons collide with an object. The X-ray generator 1 may include a filament to emit thermoelectrons and an electrode that forms a strong electric field with a high voltage.

When the high voltage generated by a high-voltage supply is applied to the X-ray generator 1, the filament serving as a cathode emits the thermoelectrons. The emitted thermoelectrons travel in a controlled direction due to the strong electric field and collide with an anode, and an X-ray is generated at the point with a small size where the thermoelectrons collide with the anode. In FIG. 2, the region represented by "S" indicates the point or region with a small size where an X-ray is generated by collision of thermoelectrons with the anode.

The X-ray irradiation region controller 10 is disposed in front of the X-ray generator 1. The X-ray generator 1 may include at least one aperture 6 to control an irradiation passage and an irradiation region of X-rays so that the X-rays are irradiated to the X-ray irradiation region controller 10.

The aperture 6 may be made of a substance such as lead or tungsten to attenuate the X-rays, but the exemplary embodiment of the present invention is not limited to this substance.

The aperture 6 may operate in a manner such that a region to which an X-ray is irradiated has the shape of a circle, similar to a photographic camera aperture.

Alternatively, a pair of members, composed of a substance capable of attenuating X-rays, are symmetrically disposed on the left and right sides of the aperture 6 relative to the X-ray irradiation central axis parallel to a longitudinal length of the X-ray generator 1, and move in an x-axis direction, that is, to the right and left relative to the aperture 6. For example, the x-axis direction extends perpendicularly out of the page of FIGS. 1-2. Another pair of members are symmetrically disposed in upper and lower sides of the aperture 6, based on the X-ray irradiation central axis and move in a y-axis direction, that is, upward and downward in a vertical direction relative to the views shown in FIGS. 1-2. As a result, the aperture 6 may operate in a manner such that the region in which X-rays are irradiated has the shape of a square or rectangle. Such a manner of control of the size of the aperture 6, through which X-rays pass, is provided only as an example and the exemplary embodiment of the present invention is not limited to this manner of control.

The irradiation passage and irradiation region of the X-rays generated by the X-ray generator 1 are controlled by the aperture 6 and the X-rays are irradiated to the X-ray irradiation region controller 10 disposed in front of the X-ray generator 1; that is, the front of the X-ray generator 1 is oriented towards the right as shown in the views of FIGS. 1-2.

The X-ray irradiation region controller 10 includes an aperture 7 to control an irradiation passage and an irradiation region of the X-rays. As described above, the aperture 7 can control an irradiation passage and an irradiation region of X-rays in the same manner as in the aperture 6 provided in the X-ray generator 1.

The camera 20 is mounted to the outside of the X-ray irradiation region controller 10 to image the object 3 present in the direction in which X-rays are irradiated.

Preferably, the camera 20 is mounted to the outside of the end of a length of the X-ray irradiation region controller 10, from which the X-rays are discharged to the outside from the X-ray irradiation region controller 10, to image at least a portion of or the entire shape of the object 3.

Figure 3:
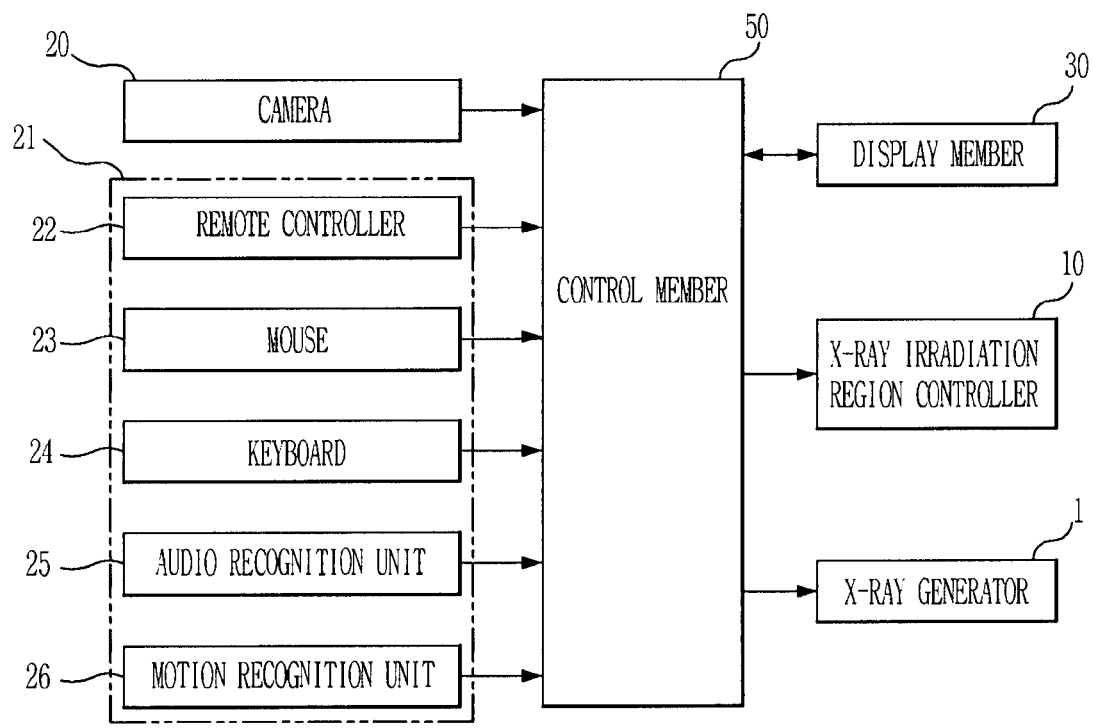
FIG. 3 is a block diagram illustrating a configuration of the X-ray device according to the exemplary embodiment of the present invention.
Figure 4:
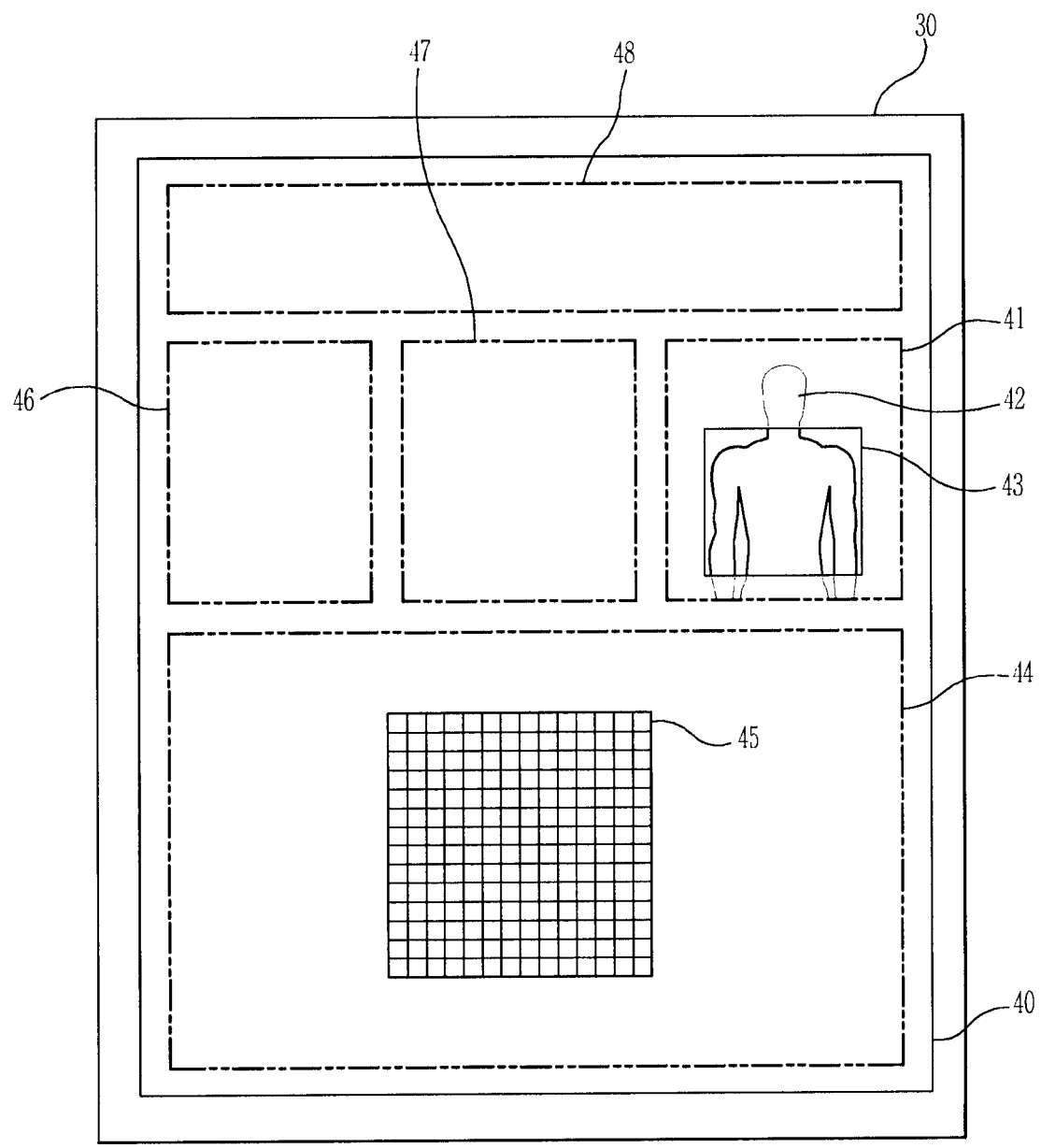
FIG. 4 is a view illustrating a user interface provided in a display member 30 according to the exemplary embodiment of the present invention.

After the camera 20 images the object 3, the image 42 of the object is displayed on the display member 30, as shown in an example screen of the display member 30 in FIGS. 3-4.

The camera 20 can image an entire or partial shape of the object 3 through control of an imaging region. When the entire shape of an object 3 is imaged, an image of the entire shape of the object 3 is displayed on the display member 30, and when the partial shape of the object is imaged, an image of the partial shape of the object 3 is displayed on the display member 30.

The detector 2 is an apparatus for detecting an amount of the X-rays that is irradiated to the X-ray irradiation region controller 10 and is then transmitted to the object 3, which detects the transmittance amount of the X-rays and thereby displays an inner state of the object 3 as an image 42.

The detector 2 may include a thin film transistor array substrate and a photosensor. However, the detector 2 may also include any known types of X-ray detectors.

Referring to FIGS. 3-4, the display member 30 provides a user of an X-ray device with a user interface 40 to output a variety of information associated with X-ray imaging of the object 3 to easily perform X-ray imaging.

The display member 30 may use a touchscreen to enable accurate X-ray imaging through a simple touch gesture of the user. The user selects an imaging region from a displayed control image, or from portions of the displayed X-ray images, controls, through the user interface 40, an X-ray irradiation region, and obtains a number of images from X-rays irradiated to the object 3 depending on the size of the X-ray irradiation region. A detailed description of the user interface 40 will be provided below.

FIG. 3 is a block diagram illustrating a configuration of the X-ray device according to the exemplary embodiment of the present invention, and FIG. 4 is a view illustrating the user interface 40 provided in a display member 30 according to the exemplary embodiment of the present invention.

The camera 20 images the object 3, and generates a corresponding image 42.

The imaging of the object 3 is performed in order to inform the user, using and controlling the X-ray device, of the X-ray irradiation region by displaying an image of a region to which X-rays are irradiated in the image 42 of the object 3 in the display member 30 such that the image of the region overlaps the image 42, which is performed through a user operation prior to main X-ray imaging.

When the object 3 is imaged, the camera 20 converts image information of the object 3 into a digital signal and transfers the digital signal to a control member 50, which may be or may include a processor such as a microprocessor or other control or computing devices. As described above, the camera 20 is mounted on the outside of the X-ray irradiation region controller 10, thus enabling the entire shape or portions of the object 3 to be imaged.

The input member 21 is an apparatus, enabling the user of the X-ray device to input a variety of instructions for overall operations to perform X-ray imaging. The user inputs instructions for X-ray imaging through the input member 21 and thus controls an overall process of X-ray imaging. The input member 21 may include at least one of a remote controller 22, a mouse 23, a keyboard 24, an audio recognition unit 25 and a motion recognition unit 26, and the like.

When the control member 50 receives the image signal transferred from the camera 20, the control member 50 outputs a signal to the display member 30 to control operation of the display member 30 in order to display the image 42 of the object 3 on the display member 30.

In addition, when the variety of instructions for X-ray imaging are input through the input member 21, the control member 50 controls operations of components constituting the X-ray device such as the display member 30, the X-ray irradiation region controller 10 and the X-ray generator 1, according to the input instructions.

The display member 30 displays the image 42 of the object 3 in one or more regions of the user interface 40 according to the signal transferred from the control member 50.

The X-ray generator 1 controls an amount of irradiated X-rays or operations of the aperture 6 according to the control signals transferred from the control member 50 to the cathode or to mechanisms controlling the aperture 6, and the X-ray irradiation region controller 10 controls operations of the aperture 7 according to the control signal transferred from the control member 50 to mechanisms controlling the aperture 7.

As can be seen from FIG. 4, the user interface 40 is divided into a plurality of regions that display different information. The image 42 of the object 3 is displayed in a first region 41 among the regions. Also, the image 42 of the object 3 is used to identify the object 3 and so may be displayed in a fifth region 48 in which basic information about the object 3, such as personal information and disease history, is displayed.

Here, respective regions of the user interface 40 will be described. The reference numbers, corresponding to respective regions, may be randomly determined and corresponding descriptions will be provided, regardless of the order of the reference numbers.

A list of parts of the object 3, such as a patient where X-ray imaging is performed, is displayed in the third region 47. For example, assuming that the object 3 is a patient, a list of body parts such as head, breast, abdomen, arms and lower body is displayed in the third region 47 and, when one of such parts is selected from the list, information of an imaging part; that is, a part which has been or which is to be imaged by X-rays, may be displayed by displaying the detailed list of the imaging parts.

The information of the imaging part may be represented by characters or icons to symbolize characteristics of respective parts. However, this is only an example and any method may be used so long as the third region 47 displays information on imaging parts. The user selects an imaging part by touching the desired imaging part among the list of imaging parts, or selects an imaging part through the input member 21 including at least one of a remote controller 22, a mouse 23, a keyboard 24, an audio recognition unit 25 and a motion recognition unit 26. Hereinafter, an example will be described in which instructions of a user are input by touch.

In the first region 41, the image 42 of the object 3 and an image 43 representing the X-ray irradiation region are displayed. At this time, the image 43 of the X-ray irradiation region is overlapped with the image 42 of the object 3 and, when an imaging part is selected in the third region 47, the image 43 of the X-ray irradiation region is displayed in a region corresponding to the imaging part.

For example, when a neck is selected as an imaging part, the image 43 of the X-ray irradiation region is displayed in the form of a square or rectangle on the image of the neck of the object 3. The image 43 of the X-ray irradiation region may be previously input to cover a predetermined region including the corresponding imaging part which is then associated with each imaging part in the list of parts in the third region 47.

The outline of the image 43 of the X-ray irradiation region may be a circle or square, or may be any known shape, and is preferably a square. The user can control the size and position of the image 43 of the X-ray irradiation region displayed in the first region 41, according to a predetermined touch gesture. That is, the user controls the size and position by touching and dragging the image 43 of the X-ray irradiation region. A detailed description associated with control of the image 43 of the X-ray irradiation region is given in the description of the second region 44 described below.

When an imaging part is selected in the third region 47 and the image 43 of the X-ray irradiation region is displayed in the image 42 of the object 3 in the first region 41 such that image 43 of the X-ray irradiation region overlaps the image 42, a second image 45 of the X-ray irradiation region is separately and only displayed in the second region 44 without displaying any object image.

The second image 45 of the X-ray irradiation region displayed in the second region 44 may be wider than the image 43 of the X-ray irradiation region displayed in the first region 41 and may be displayed together with gradations indicating size. This enables the user to easily control the images 43, 45 of the X-ray irradiation region.

The user can control an irradiation region of X-rays irradiated to the object 3 by controlling the image 43 of the X-ray irradiation region displayed in the first region 41, or by controlling the image 45 of the X-ray irradiation region displayed in the second region 44 according to a user selection, which may be based on the user's taste and convenience. Accordingly, the user interface 50 is a graphic user interface (GUI), such that manipulation of the images 43, 45 are processed by the control member 50 to generate control signals for controlling the X-ray irradiation region controller 10 in a manner known in the art, for example, to direct the X-ray irradiation region controller 10 to adjust the direction of irradiated X-rays and to control the size of the aperture 7 to determine the corresponding size, shape, direction, and orientation of the X-ray irradiation region relative to the object 3 and the detector 2.

The user can control the size and position of the second image 45 of the X-ray irradiation region displayed in the second region 44 according to a predetermined touch gesture. That is, the user can control the size and position by touching and dragging the image 45 of the X-ray irradiation region.

When the size and position of the second image 45 of the X-ray irradiation region are changed in the second region 44 by a touch gesture, the image 43 of the X-ray irradiation region of the first region 41 also undergoes changes in size and position thereof while overlapping the image 42 of the object 3.

That is, the image 43 of the X-ray irradiation region displayed to be overlapped with the image 42 of the object 3 in the first region 41 is changed according to a change of the second image 45 of the X-ray irradiation region displayed in the second region 44 and, as a result, the user can accurately and finely control an imaging part of the object 3 to which X-rays are irradiated and imaging is performed.

On the other hand, when the image 43 of the X-ray irradiation region displayed in the first region 41 is controlled, the second image 45 of the X-ray irradiation region displayed in the second region 44 may also be controlled.

FIGS. 5A-5H are various views illustrating states and changes in states of images representing the X-ray irradiation region, and in turn to control and shape the X-ray irradiation region, in which the size, position and shape of the second image 45 of the X-ray irradiation region displayed in the second region 44 of the user interface 40 of the display member 30 are controlled according to a predetermined touch gesture.

In FIGS. 5A-5H, a single circle filled with black represents a touch point and an empty single circle represents a point at which the touched black single circle will be dragged and positioned. An arrow expressed by a broken line represents a movement route and a double circle in which a larger circle surrounds the single circle filled with black represents a double touch point.

Figure 5A:
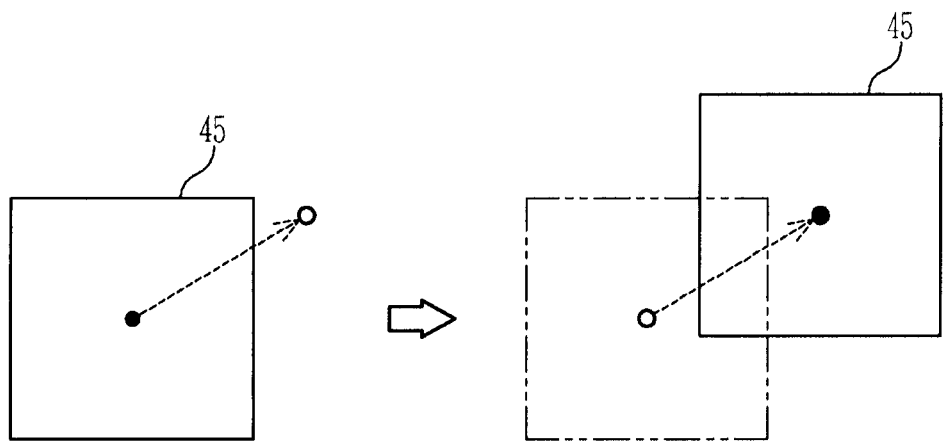
FIGS. 5A-5H are various views illustrating states and changes in states of the X-ray irradiation region, in which the size, position and shape of an image representing the X-ray irradiation region displayed in a region of a display member are controlled according to a predetermined touch gesture.

FIG. 5A illustrates an example of a touch gesture to move the second image 45 of the X-ray irradiation region. The user can move the second image 45 of the X-ray irradiation region to a desired position by simultaneously touching and dragging a given point inside the second image 45 of the X-ray irradiation region.

Figure 5B:
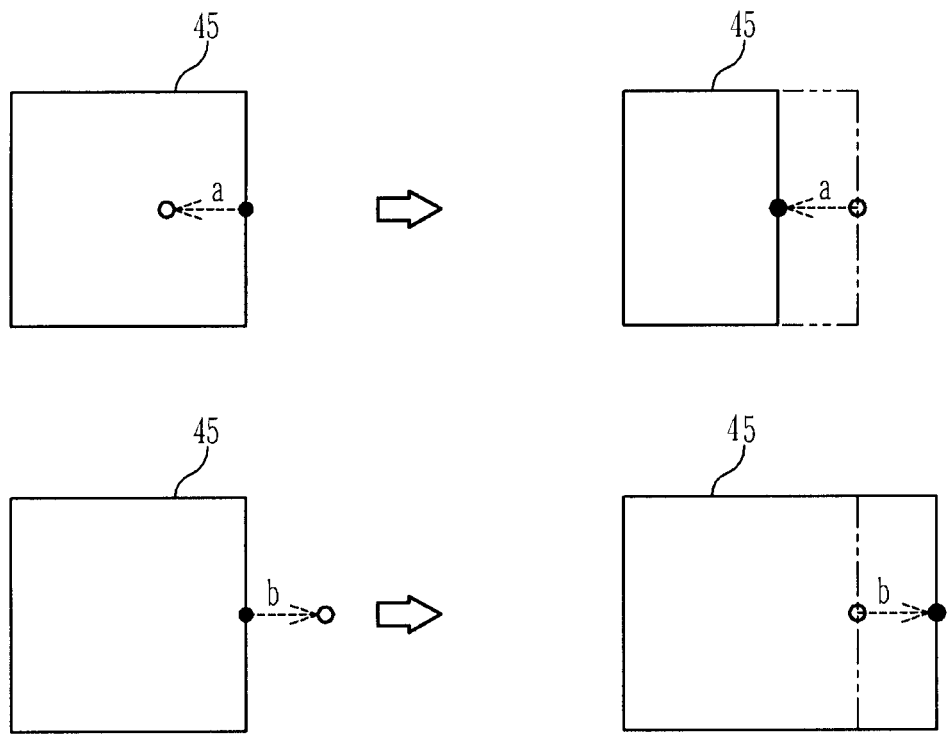
Figure 5C:
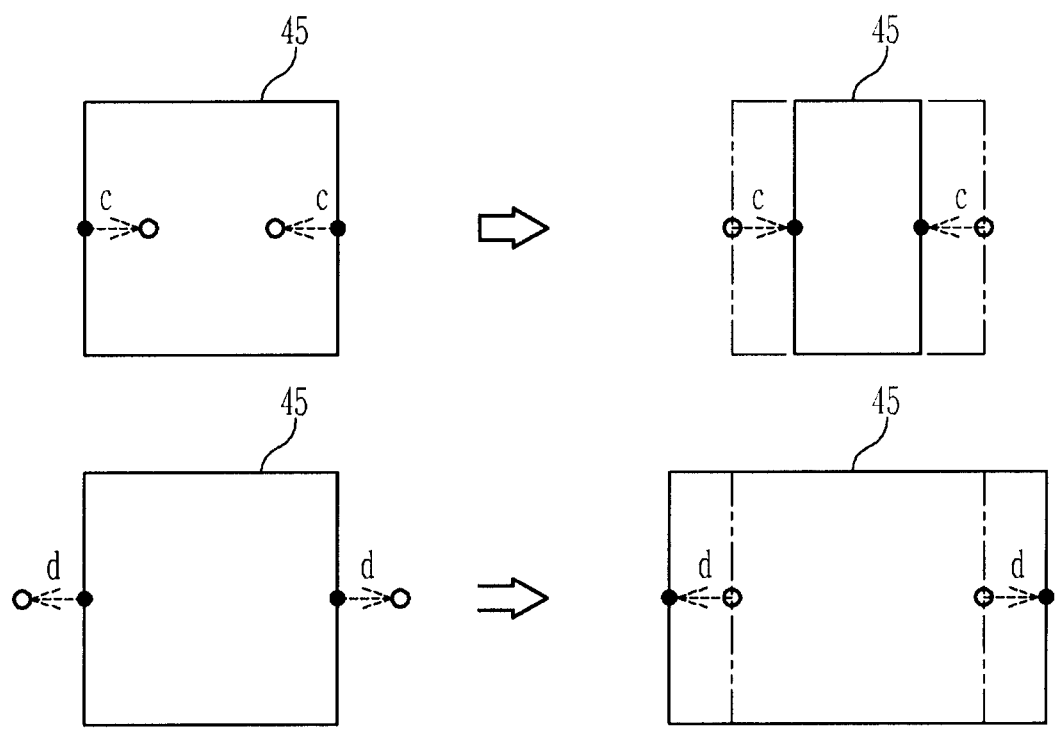
Figure 5D:
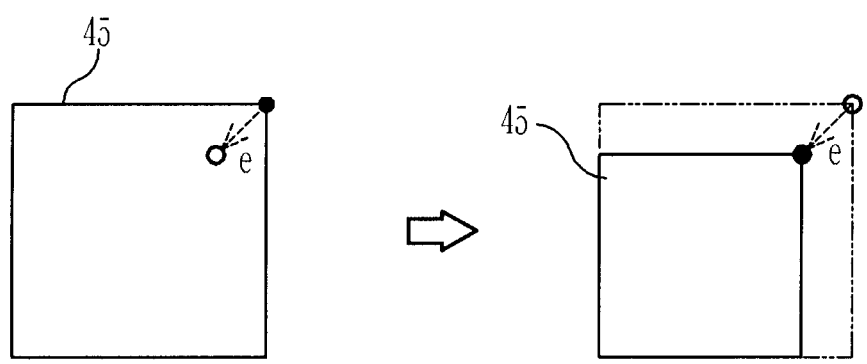
Figure 5D:
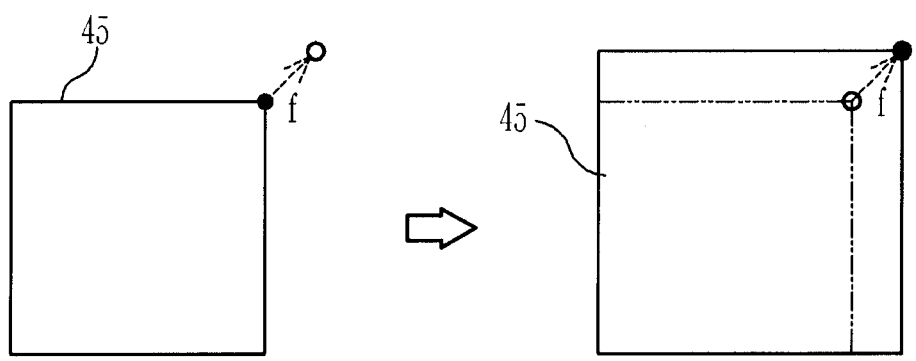

FIGS. 5B, 5C and 5D illustrate an example of a touch gesture to change the size of the second image 45 of the X-ray irradiation region.

As shown in FIG. 5B, the user controls the size of the second image 45 of the X-ray irradiation region by touching and dragging a given point of one side of the second image 45. When a given point of one side of the second image 45 is touched and dragged toward a facing side (in the "a" direction), the size of the second image 45 can be decreased and, when the point is dragged toward an opposite direction to the facing side (in the "b" direction), the size of the image 45 can be increased.

In addition, as shown in FIG. 5C, the user controls the size of the image 45 by touching and dragging given points of two facing sides of the image 45. When the user touches given points of two facing sides of the image 45 and drags such that the points face each other and become closer (in the "c" direction), the size of the image 45 can be decreased, and when the user drags such that the two points are opposite to each other and become farther apart (in the "d" direction), the size of the image 45 can be increased.

In addition, as shown in FIG. 5D, the user can control the size of image 45 by touching a given vertex of the image 45 and dragging in a diagonal line direction. When the user touches a vertex of the image 45 and drags toward a vertex of a facing diagonal line direction (in the "e" direction), the size of the image 45 can be decreased while the original shape thereof can be maintained, on the other hand, when the user drags toward an opposite side to the diagonal line direction (the "f" direction), the size of the image 45 can be increased, while the original shape thereof can be maintained. As described above, touch gestures shown in FIGS. 5B, 5C and 5D are provided only as examples of touch gestures capable of controlling the size of the second image 45 of the X-ray irradiation region and other touch gestures to realize the same functions may also be used.

Figure 5E:
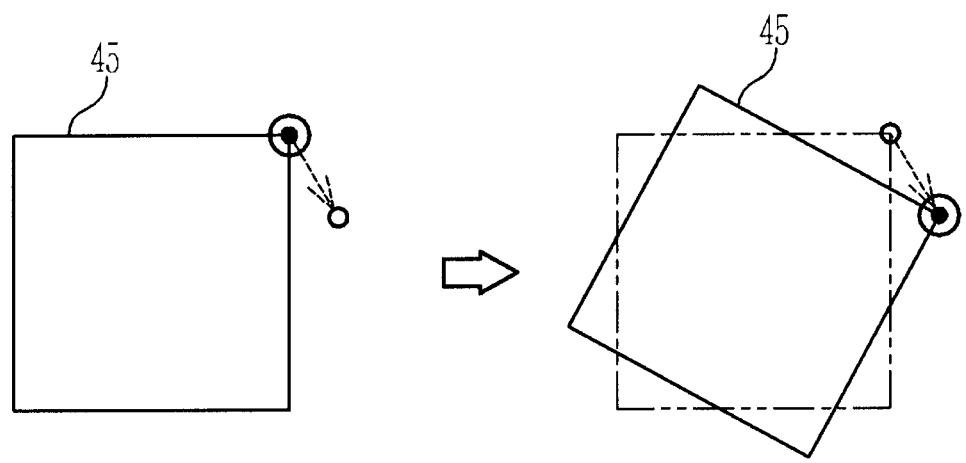
Figure 5F:
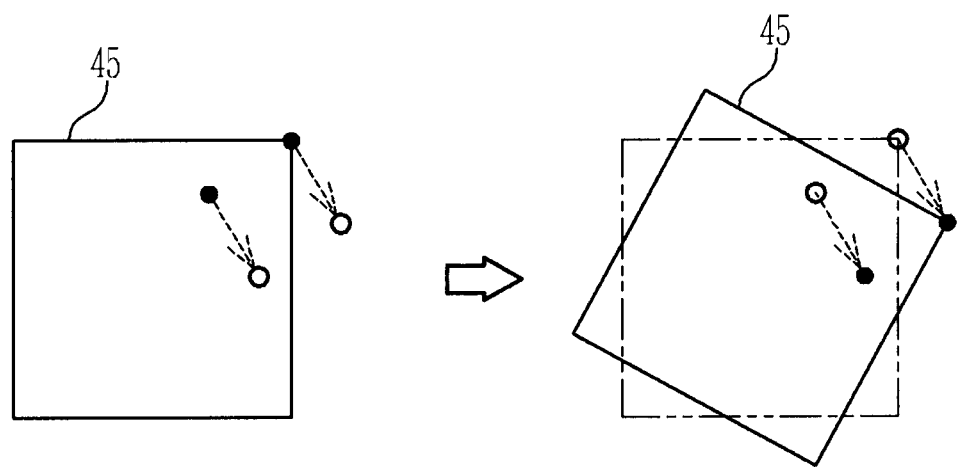

FIGS. 5E and 5F illustrate an example of a touch gesture to rotate the second image 45 of the X-ray irradiation region.

As shown in FIG. 5E, the user can rotate the image 45 by continuously touching a vertex of the image 45 twice and dragging the image 45 to a desired rotation direction. At this time, the image 45 rotates at the same place and does not move; that is, the image 45 rotates about a central point, and does not have any translational movement.

In addition, as shown in FIG. 5F, the user can rotate the image 45 by touching a given vertex of the image 45 and a given point in the image 45 and dragging the image 45 in a rotation direction. Similar to FIG. 5E, the image rotates at the same place and does not move; that is, the image 45 rotates about a central point, and does not have any translational movement. As described above, the touch gestures shown in FIGS. 5E and 5F are provided only as examples of touch gestures capable of controlling the size and orientation of the image 45 and other touch gestures to realize the same functions may also be used.

Figure 5G:
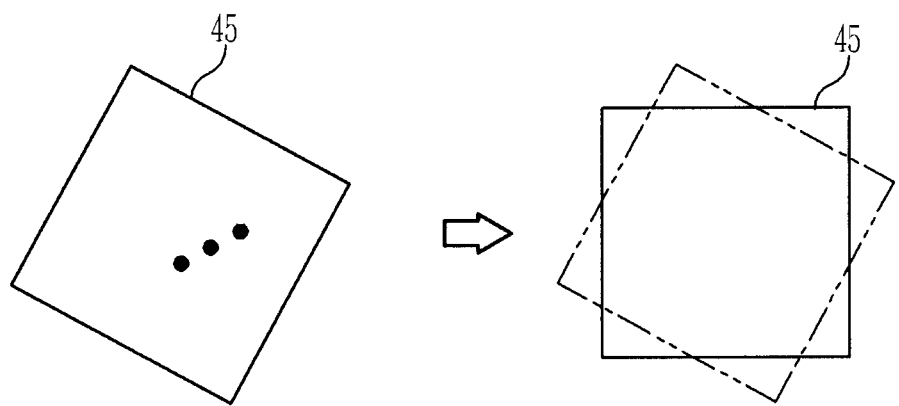
Figure 5H:
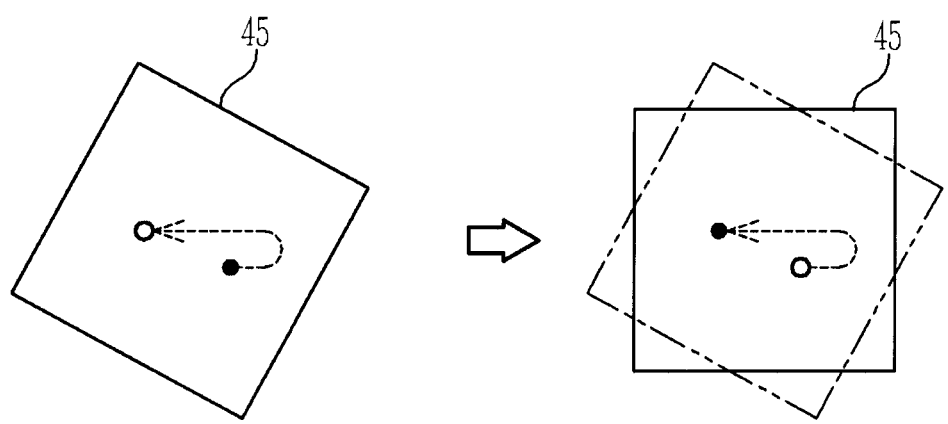

FIGS. 5G and 5H illustrate an example of a touch gesture to initialize the second image 45 of the X-ray irradiation region to the state before the size, position and shape thereof are changed.

As shown in FIG. 5G, when the user simultaneously touches three points in the image 45, the image 45 is initialized to the state before the size, position and shape thereof are changed.

In addition, as shown in FIG. 5H, when the user touches a given point in the image 45, drags the point in one direction, and then drags the point in an opposite direction, the image 45 is initialized to the state before the size, position and shape thereof are changed. In FIG. 5H, shaking of the image 45 is illustrated, but is provided only as an example. The image 45 is initialized when shaken, regardless of direction.

A description of additional features of the present invention associated with FIG. 4 will be given.

The size of the X-ray irradiation region and an amount of irradiated X-rays estimated based on the size of the X-ray irradiation region are displayed in the fourth region 46. The size of the X-ray irradiation region can be determined through data of an area in which imaging is mainly performed in each imaging part of the object 3.

The amount of irradiated X-rays depending on the size of the X-ray irradiation region can be determined by calculating the amount of X-rays depending on the size of the X-ray irradiation region using an amount of X-rays generally irradiated during X-ray imaging.

For example, when a breast of a patient, as the object 3, is selected as the X-ray imaging region, information such as an imaging area in which imaging is mainly performed on the breast and an amount of irradiated X-rays is displayed as a list in the fourth region 46.

In addition, variation in the amount of irradiated X-rays by control of the X-ray irradiation region is displayed in real-time. The user can assume, determine, or estimate a value of an amount of X-rays irradiated to the object 3 depending on the area of the X-ray irradiation region based on this information and control the size of the X-ray irradiation region based on the assumed or estimated value. For example, when the user considers an amount of assumed or estimated X-rays irradiated to the selected X-ray irradiation region to be high, the user can reduce an amount of irradiated X-rays by decreasing the size of the X-ray irradiation region.

Information about the object 3 is displayed in the fifth region 48. When the object 3 is a patient, information such as personal information and disease history of the patient is displayed which helps the user of the X-ray device to perform X-ray imaging. The position of each region in the user interface 40 shown in FIG. 4 is provided only as an example and may be changed.

Figure 6:
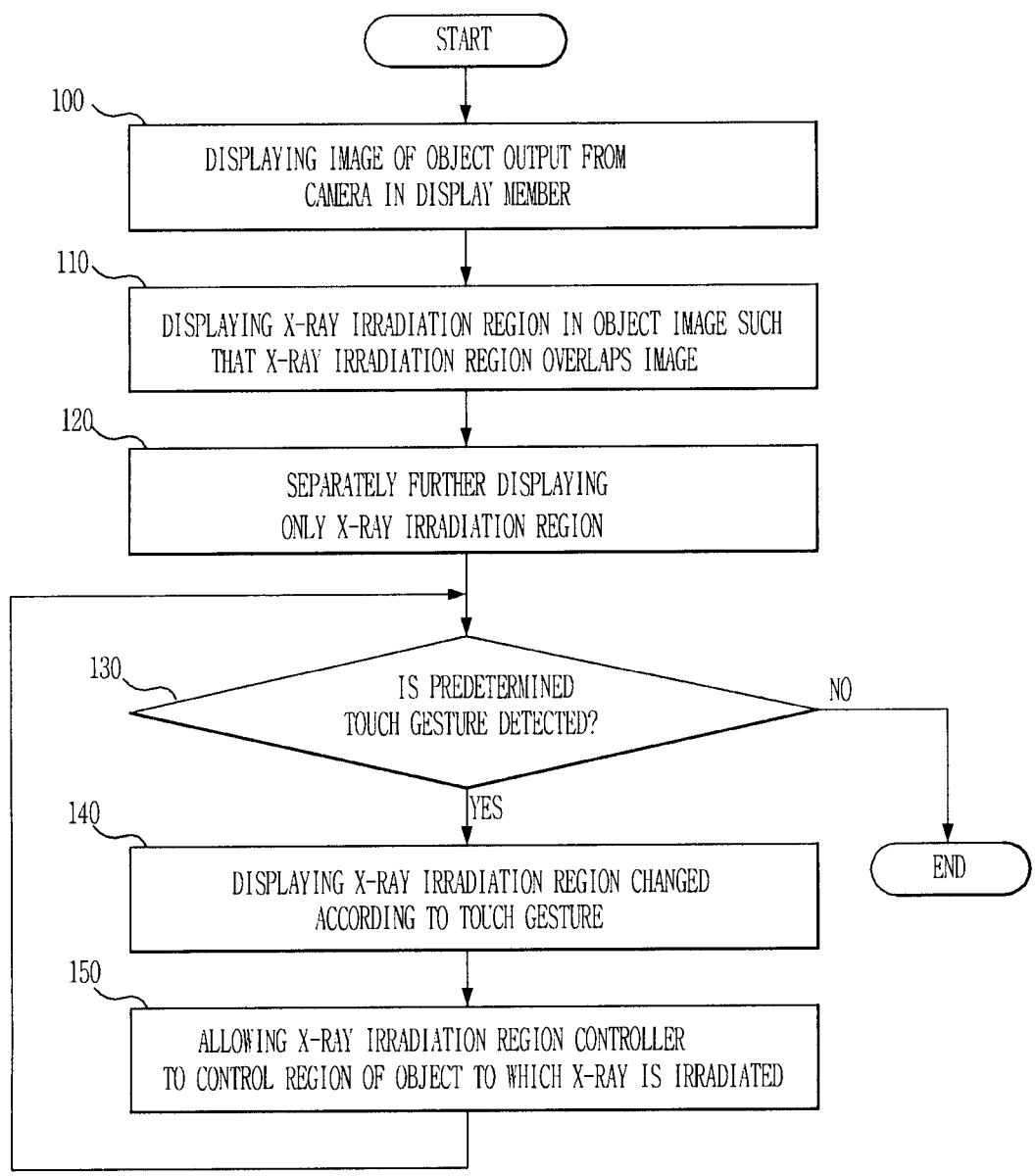
FIG. 6 is a flowchart illustrating a method for controlling an X-ray irradiation region of the X-ray device according to the exemplary embodiment of the present invention.

FIG. 6 is a flowchart illustrating a method for controlling an X-ray irradiation region of the X-ray device according to the exemplary embodiment of the present invention.

Referring to FIG. 6, when the object 3 is imaged using the camera 20, the control member 50 displays the image 42 of the object in the display member 30 in step 100.

When the object 3 is imaged, the camera 20 converts image information of the object 3 into a digital signal and transfers the digital signal to a control member 50. The control member 50 receives the image signal of the object 3 transferred from the camera 20 and outputs, to the display member 30, a signal to control operation of the display member 30 in order to display the image 42 of the object in the display member 30. The display member 30 displays the image 42 of the object 3 in the first region 41 of the user interface 40 according to the signal transferred from the control member 50. The control member 50 may further display an image representing an X-ray irradiation region capable of guiding control of the X-ray irradiation region, when the image 42 of the object is displayed in the display member 30.

When the image 42 of the object 3 is displayed in the user interface 40 of the display member 30, the control member 50 displays the image 43 of the X-ray irradiation region in the image 42 of the object such that the image 43 of the X-ray irradiation region overlaps the image 42 in step 110.

When information about the imaging part of the object 3 is input after the image 42 of the object 3 is displayed on the user interface 40 of the display member 30, the control member 50 displays the image 43 of the X-ray irradiation region overlapped in a region corresponding to the imaging part. The image of the X-ray irradiation region may be previously input to be associated with each imaging part to cover a predetermined region including the corresponding imaging part.

The control member 50 separately displays only a second image 45 representing the X-ray irradiation region in the second region 44 of the user interface 40 of the display member 30 in step 120. When the image 42 of the object is overlapped with the image 43 of the X-ray irradiation region in the first region 41 of the user interface 40 of the display member 30, only the second image 45 is displayed in the second region 44 without the image 42 of the object 3.

When the second image 45 is displayed in the second region 44 of the user interface 40 of the display member 30, the control member 50 confirms whether the predetermined touch gesture is detected in the X-ray irradiation region 45 displayed in the second region 44 in step 130. If no predetermined touch gesture in detected in step 130, the method ends.

Otherwise, the second image 45 of the X-ray irradiation region displayed in the second region 44 undergoes variation in size and position according to a predetermined touch gesture in step 140. That is, the user can adjust the image 45 of the X-ray irradiation region to the desired size and position according to the predetermined touch gesture.

When the predetermined touch gesture is detected in the image 45 of the X-ray irradiation region displayed in the second region 44, the control member 50 displays the image 45 changed according to the corresponding touch gesture in the second region 44 in step 140.

When one of the touch gestures described with reference to FIGS. 5A-5H is input by a user using the exposed outside surface of the touch screen, the control member 50 confirms whether or not the corresponding touch gesture is the same as the predetermined touch gesture, and when the corresponding touch gesture is the same as the predetermined touch gesture, controls the size and position of the image 45 according to the corresponding touch gesture and displays the modified image 45. When the size and position of the image 45 are changed by the touch gesture in the second region 44, the size and position of the image 43 of the first region 41 are also changed in a state that the image 43 overlaps the image 42 of the object 3. That is, the image 43 of the X-ray irradiation region overlapping the image 42 of the object 3 in the first region 41 is changed according to a change of the second image 45 of the X-ray irradiation region displayed in the second region 44 and, as a result, the user can accurately and finely control an imaging part of the object 3 in which an X-ray is irradiated and imaging is performed. Although, hereinbefore, control of the second image 45 of the X-ray irradiation region displayed in the second region 44 has been described in one example, the image 43 of the X-ray irradiation region displayed in the first region 41 may also be controlled, and when the image 43 displayed in the first region 41 is controlled, the second image 45 displayed in the second region 44 may also be controlled.

When the second image 45 of the X-ray irradiation region displayed in the second region 44 is changed according to a predetermined touch gesture, the control member 50 controls the X-ray irradiation region controller 10 so that the region of the object 3 in which X-rays are irradiated corresponds to the image 45 of the X-ray irradiation region displayed in the second region 44 in step 150, and the method loops back to step 130.

The control member 50 controls operation of the aperture 7 of the X-ray irradiation region controller 10 by outputting, to the X-ray irradiation region controller 10, a signal to control the X-ray irradiation region controller 10 and thereby, to make the region of X-rays irradiated to the object 3 correspond to the second image 45 of the X-ray irradiation region varied in the second region 44.

Since the touch gesture may be continued until a user-desired X-ray irradiation region is formed having a desired size and position, the control member 50 repeats steps 130 to 150 in FIG. 6 until the touch gesture is not detected in the second image 45 of the X-ray irradiation region of the second region 44.

In the step 130, when the predetermined touch gesture is not detected anymore in the image of the X-ray irradiation region displayed in the second region 44, control of the X-ray irradiation region is considered to be completed and the control operation is finished.

Figure 7:
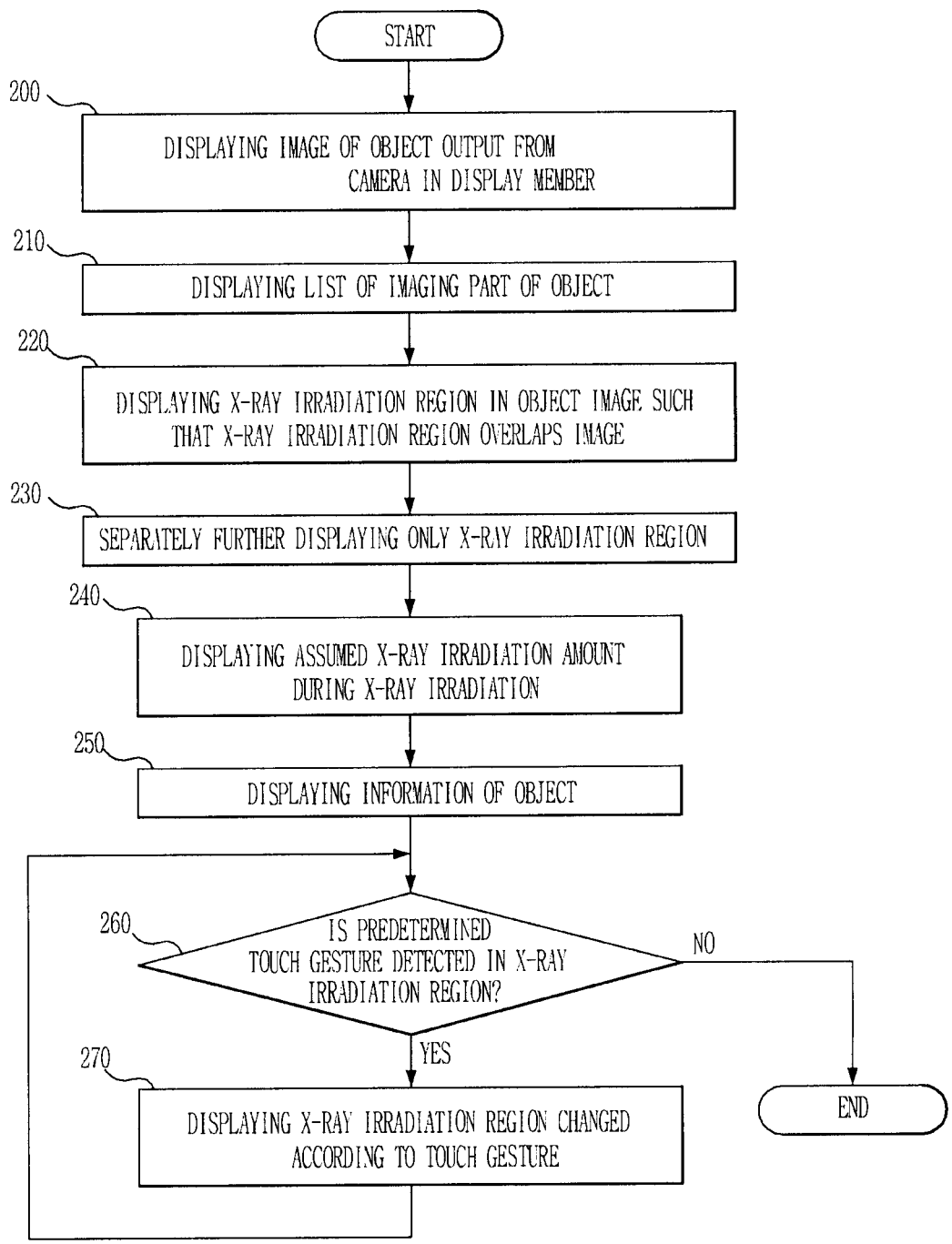
FIG. 7 is a flowchart illustrating a method for displaying an X-ray image according to the embodiment of the present invention.

FIG. 7 is a flowchart illustrating a method for displaying an X-ray image according to the exemplary embodiment of the present invention.

Referring to FIG. 7, when the object 3 is imaged using the camera 20, the control member 50 displays the image 42 of the object 3 on the display member 30 in step 200.

When the object 3 is imaged, the camera 20 converts image information of the object 3 into a digital signal and transfers the digital signal to the control member 50. The control member 50 receives the image signal of the object 3 transferred from the camera 20 and outputs, to the display member 30, a signal to control operation of the display member 30 in order to display the image 42 of the object 3 in the display member 30. The display member 30 displays the image 42 of the object 3 in the first region 41 of the user interface 40 according to the signal transferred from the control member 50.

The control member 50 displays a list of imaging parts of the object 3 in the display member 30 in step 210.

The list of imaging parts, in which X-ray imaging is performed, is displayed in the third region 47 of the user interface 40 of the display member 30. For example, assuming that the object 3 is a patient, a list of body parts such as head, breast, abdomen, arms and lower body is displayed in the third region 47 and, when one of the body parts is selected from the list, information of the imaging part may be displayed by displaying the detailed list of the imaging parts.

The information of the imaging parts may be represented by characters or icons to symbolize characteristics of respective parts. However, this is only an example and any method may be used so long as the method displays information of imaging parts.

The control member 50 displays the image 43 of the X-ray irradiation region in the image 42 of the object 3 such that the image 43 of the X-ray irradiation region overlaps the image 42 of the object in step 220.

When information of the imaging part of the object 3 is input after the image 42 of the object 3 is displayed in the user interface 40 of the display member 30, the control member 50 displays the image 43 of the X-ray irradiation region in a region corresponding to the imaging part such that the image 43 of the X-ray irradiation region overlaps the imaging part region. The image 43 may be previously input, for each imaging part, to cover a predetermined region including the corresponding imaging part.

The control member 50 separately displays only the second image 45 of the X-ray irradiation region in the second region 44 of the user interface 40 of the display member 30 in step 230. When the image 42 of the object is displayed with the image 43 of the X-ray irradiation region in the first region 41 of the user interface 40 of the display member 30 such that the image 43 of the X-ray irradiation region overlaps the first region 41, only the second image 45 of the X-ray irradiation region is displayed in the second region 44 without displaying the image 42 of the object 3.

The control member 50 displays a value of an assumed or estimated amount of X-rays irradiated to the fourth region 46 in the user interface 40 of the display member 30 in step 240.

The size of the X-ray irradiation region and the value of an amount of irradiated X-rays estimated based on the size are displayed in the fourth region 46. The size of the X-ray irradiation region can be determined through data of an area in which imaging is mainly performed in each imaging part of the object 3.

The amount of irradiated X-rays can be determined by calculating the amount of X-rays depending on the size of the X-ray irradiation region using an amount of X-rays generally irradiated in X-ray imaging.

In addition, variation in the amount of irradiated X-rays with control of the X-ray irradiation region is displayed in real-time. The user can assume or estimate a value of an amount of X-rays irradiated to the object 3 depending on the area of the X-ray irradiation region based on this information and control the size of the X-ray irradiation region based on the assumed or estimated value. For example, when the user considers an amount of assumed or estimated X-rays irradiated to the selected X-ray irradiation region to be high, the user can reduce an amount of irradiated X-rays by decreasing the X-ray irradiation region.

The control member 50 displays information associated with the object 3 in the fifth region 48 of the user interface 40 of the display member 30 in step 250.

When the object 3 is a patient, information such as personal information and disease history of the patient is displayed and helps the user of the X-ray device to perform X-ray imaging.

When the second image 45 of the X-ray irradiation region is displayed in the second region 44 of the user interface 40 of the display member 30, the control member 50 confirms whether the predetermined touch gesture is detected in the second image 45 of the X-ray irradiation region displayed in the second region 44 in step 260. If no predetermined touch gesture is detected, the method ends.

Otherwise, the second image 45 of the X-ray irradiation region displayed in the second region 44 undergoes variations in size and position according to a predetermined touch gesture. That is, the user can obtain the desired size and position of the image 45 of the X-ray irradiation region according to the predetermined touch gesture.

When the predetermined touch gesture is detected in the image 45 of the X-ray irradiation region displayed in the second region 44, the control member 50 displays the image 45 of the X-ray irradiation region changed according to the corresponding touch gesture in the second region 44 in step 270, and loops back to step 260.

When the touch gesture described with reference to FIGS. 5A-5H is input by a user using the exposed outside surface of the touch screen, the control member 50 confirms whether or not the corresponding touch gesture is the same as the predetermined touch gesture, and when the corresponding touch gesture is the same as the predetermined touch gesture, the control member 50 controls the size and position of the image 45 of the X-ray irradiation region according to the corresponding touch gesture and displays the modified image 45 of the X-ray irradiation region. When the size and position of the image 45 of the X-ray irradiation region are changed by the touch gesture in the second region 44, the size and position of the image 43 of the X-ray irradiation region of the first region 41 are also changed in a state that the image 43 of the X-ray irradiation region overlaps the image 42 of the object 3. That is, the image 43 of the X-ray irradiation region overlapping the image 42 of the object in the first region 41 is changed according to a change of the image 45 of the X-ray irradiation region displayed in the second region 44 and, as a result, the user can accurately and finely control an imaging part of the object 3 in which X-rays are irradiated and imaging is performed. Although, hereinbefore, control of the image 45 of the X-ray irradiation region displayed in the second region 44 has been described as one example, the image 43 of the X-ray irradiation region displayed in the first region 41 may be controlled, and when the image 43 of the X-ray irradiation region displayed in the first region 41 is controlled, the image 45 of the X-ray irradiation region displayed the second region 44 may also be controlled.

Since the touch gesture may be continued until a user-desired X-ray irradiation region is formed, the control member 50 repeats steps 260 to 270 until the touch gesture is not detected in the image 45 of the X-ray irradiation region of the second region 44.

In the step 260, when the predetermined touch gesture is not detected anymore in the image 45 of the X-ray irradiation region displayed in the second region 44, the control of the image 45 of the X-ray irradiation region is considered to be completed and the control operation is finished.

The above-described apparatus and methods according to the present invention can be implemented in hardware, firmware or as software or computer code that can be stored in a recording medium such as a CD ROM, a RAM, a ROM, a floppy disk, DVDs, a hard disk, a magnetic storage media, an optical recording media, or a magneto-optical disk or computer code downloaded over a network originally stored on a remote recording medium, a computer readable recording medium, or a non-transitory machine readable medium and to be stored on a local recording medium, so that the methods described herein can be rendered in such software that is stored on the recording medium using a general purpose computer, a digital computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An X-ray device comprising:
    a camera configured to image an object and output the image of the object;
    a display member configured to display the image of the object and an image of an X-ray irradiation region of the object;
    an X-ray irradiation region controller configured to control the X-ray irradiation region of the object to which X-rays are irradiated; and
    a control member configured to enable the X-ray irradiation region controller to control the X-ray irradiation region, based on the image of the X-ray irradiation region displayed in the display member,
    wherein the display member displays the image of the X-ray irradiation region as a first image in the image of the object output from the camera such that the first image of the X-ray irradiation region overlaps the image of the object, and
    wherein the display member further displays a second image of the X-ray irradiation region, in addition to the first image of the X-ray irradiation region to be overlapped with the image of the object, such that the first image of the X-ray irradiation region overlapped with the image of the object is changed according to a change of the second image of the X-ray irradiation region.

2. The X-ray device according to claim 1, wherein the X-ray irradiation region is determined based on the image of the X-ray irradiation region displayed in the display member in response to a user instruction.

3. The X-ray device according to claim 2, wherein the user instruction comprises an instruction input through a touch of the image of the X-ray irradiation region displayed in the display member.

4. The X-ray device according to claim 2, wherein the user instruction comprises an instruction input through at least one of a remote controller, a mouse, an input device, an audio recognition unit and a motion recognition unit.

5. The X-ray device according to claim 1, wherein the display member includes a touchscreen and displays a plurality of information for guiding an X-ray imaging of the object in a plurality of regions on the touchscreen, respectively.

6. The X-ray device according to claim 1, wherein the display member displays a previously input list of X-ray imaging parts of the object in order to allow a user to select one of the X-ray imaging parts of the object.

7. The X-ray device according to claim 1, wherein the display member displays a value representing an estimated amount of irradiated X-rays determined according to a size of the X-ray irradiation region.

8. The X-ray device according to claim 1, wherein the camera directly images the object in a region larger than the X-ray irradiation region.

9. The X-ray device according to claim 1, wherein the display member is further configured to display the image of the object and an image of the X-ray irradiation region of the object before the X-rays are irradiated to the object.

10. The X-ray device according to claim 1, wherein when an user instruction to adjust a size and position of the image of the X-ray irradiation region is received by the control member, the control member is further configured to control the size and position of the image of the X-ray irradiation region in accordance with the user instruction, to enable the display member to display the image of the X-ray irradiation region that has the controlled size and position and to enable the X-ray irradiation region controller to control the X-ray irradiation region of the object to which the X-rays will be irradiated based on the controlled size and position of the image of the X-ray irradiation region.

11. The X-ray device according to claim 1, wherein the camera is mounted to an outside of an aperture of the X-ray irradiation region controller.

12. A method for controlling an X-ray irradiation region comprising:
    displaying an image of an object obtained by a camera of an X-ray device in a display member of the X-ray device;
    displaying an image of an X-ray irradiation region in the display member displaying the obtained image of the object; and
    controlling a region of the object to which X-rays are irradiated, based on the image of the X-ray irradiation region displayed in the display member,
    wherein the displaying the image of the X-ray irradiation region comprises:
    displaying the image of the X-ray irradiation region as a first image in the image of the object output from the camera such that the first image of the X-ray irradiation region overlaps the image of the object; and displaying a second image of the X-ray irradiation region, in addition to the first image of the X-ray irradiation region to be overlapped with the image of the object, such that the first image of the X-ray irradiation region overlapped with the image of the object is changed according to a change of the second image of the X-ray irradiation region.

13. The method according to claim 12, wherein the controlling of the region of the object to which X-rays are irradiated, based on the image of the X-ray irradiation region displayed in the display member, is carried out by controlling the image in response to a user instruction.

14. The method according to claim 13, wherein the user instruction comprises an instruction input through a touch of the image of the X-ray irradiation region displayed in the display member.

15. The method according to claim 13, wherein the user instruction comprises an instruction input through at least one of a remote controller, a mouse, an input device, an audio recognition unit and a motion recognition unit.

16. The method according to claim 12, wherein a value representing an estimated amount of irradiated X-rays is displayed according to a size of the X-ray irradiation region, when the X-ray irradiation region is displayed.

17. The X-ray device according to claim 12, wherein the display member includes a touchscreen and display a plurality of information guiding X-ray imaging of the object in a plurality of regions on the touchscreen, respectively.

18. The method according to claim 12, wherein the controlling of the region of the object to which an X-ray is irradiated, based on the image of the X-ray irradiation region displayed in the display member, is carried out by displaying the image of the X-ray irradiation region controlled by a user instruction on the object image displayed in the display member such that the image of the X-ray irradiation region overlaps the object image and then by controlling the region of the object to which X-rays are irradiated.

19. The method according to claim 18, wherein the X-ray irradiation region is controlled to be in a different area from an initially set area to control the irradiation region by displaying the image of the X-ray irradiation region controlled by the user instruction on the object image displayed in the display member such that the image of the X-ray irradiation region overlaps the object image.

20. The method according to claim 12, wherein, when the image of the object obtained by the camera of the X-ray device is displayed in the display member of the X-ray device, the image of the X-ray irradiation region to guide control of the X-ray irradiation region is separately displayed.

21. The method according to claim 12, wherein the camera directly images the object in a region larger than the X-ray irradiation region.

* * * * *